US009271847B2

(12) United States Patent
Murphy

(10) Patent No.: US 9,271,847 B2
(45) Date of Patent: Mar. 1, 2016

(54) SYSTEM AND METHOD FOR FACILITATING HIP SURGERY

(76) Inventor: Stephen B. Murphy, Winchester, MA (US)

( * ) Notice: Subject to any disclaimer, the term of this patent is extended or adjusted under 35 U.S.C. 154(b) by 1373 days.

(21) Appl. No.: 13/008,547

(22) Filed: Jan. 18, 2011

(65) Prior Publication Data
US 2011/0112589 A1 May 12, 2011

Related U.S. Application Data

(62) Division of application No. 11/351,455, filed on Feb. 10, 2006, now Pat. No. 7,885,705.

(51) Int. Cl.
*A61B 5/05* (2006.01)
*A61F 2/46* (2006.01)
*A61B 5/103* (2006.01)
(Continued)

(52) U.S. Cl.
CPC .............. *A61F 2/4607* (2013.01); *A61B 5/103* (2013.01); *A61B 5/4528* (2013.01); *A61B 19/5244* (2013.01); *A61F 2/4657* (2013.01); *A61B 5/6878* (2013.01); *A61B 2019/461* (2013.01); *A61B 2019/508* (2013.01); *A61B 2019/5255* (2013.01); *A61B 2019/5483* (2013.01); *A61F 2/36* (2013.01); *A61F 2/4684* (2013.01); *A61F 2002/4632* (2013.01); *A61F 2002/4658* (2013.01); *A61F 2002/4668* (2013.01)

(58) Field of Classification Search
USPC ............. 600/407; 606/53, 81, 88–89, 85, 264
See application file for complete search history.

(56) References Cited

U.S. PATENT DOCUMENTS 5,122,146 A * 6/1992 Chapman et al. ............. 606/102
5,324,293 A 6/1994 Rehmann
(Continued)

FOREIGN PATENT DOCUMENTS

WO WO-02/067784 A2 9/2002
WO WO-02/080824 A 10/2002
(Continued)

OTHER PUBLICATIONS

"Acetabular Fractures," http://www.amirmd.com/ortho-info/acetabularfx.html site visited Feb. 16, 2006.
(Continued)

*Primary Examiner* — Joel F Brutus
(74) *Attorney, Agent, or Firm* — Cesari and McKenna LLP; Michael R. Reinemann

(57) ABSTRACT

A system and method for use during hip surgery includes a position frame that is removably secured to the patient's femur. The system further includes a tracking unit and navigation engine that establish a pelvic coordinate system and, with the patient's leg placed in a predetermined orientation, capture the location of the femoral position frame within the pelvic coordinate system. The system further includes an image generator configured to display one or more images for directing the surgeon to return the patient's leg to the predetermined orientation following a trial reduction based upon the previously captured position. A leg change determination engine compares the current, post-reconstruction position of the femoral position tracking frame with the previously captured, pre-reconstruction position to derive leg length, offset, and anterior-posterior change values. The change values are then provided to the surgeon for evaluating the suitability of the trial reduction.

18 Claims, 7 Drawing Sheets

(51) Int. Cl.
*A61B 5/00* (2006.01)
*A61B 19/00* (2006.01)
*A61F 2/36* (2006.01)

(56) References Cited

U.S. PATENT DOCUMENTS

| | | | |
|---|---|---|---|
| 6,096,050 | A | 8/2000 | Audette |
| 6,236,875 | B1 | 5/2001 | Bucholz et al. |
| 6,490,467 | B1 | 12/2002 | Bucholz et al. |
| 6,640,127 | B1 | 10/2003 | Kosaka et al. |
| 6,711,431 | B2 | 3/2004 | Sarin et al. |
| 2002/0035321 | A1 | 3/2002 | Bucholz et al. |
| 2002/0115934 | A1 | 8/2002 | Tuke |
| 2002/0147455 | A1 | 10/2002 | Carson |
| 2003/0153829 | A1* | 8/2003 | Sarin et al. ............... 600/426 |
| 2004/0068260 | A1* | 4/2004 | Cossette et al. .......... 606/63 |
| 2004/0102792 | A1 | 5/2004 | Sarin et al. |
| 2004/0143340 | A1 | 7/2004 | Tuma et al. |
| 2004/0153062 | A1 | 8/2004 | McGinley et al. |
| 2005/0021037 | A1* | 1/2005 | McCombs et al. ......... 606/79 |
| 2005/0065617 | A1* | 3/2005 | Moctezuma de la Barrera et al. ........................ 623/908 |
| 2005/0119566 | A1 | 6/2005 | Sasso |

FOREIGN PATENT DOCUMENTS

| | | |
|---|---|---|
| WO | WO-2004/001569 A2 | 12/2003 |
| WO | WO-2005/000140 A | 1/2005 |

OTHER PUBLICATIONS

Bell, Alexander L. et al. "A Comparison of the Accuracy of Several Hip Center Location Prediction Methods" J. Biomechanics vol. 23, No. 6 pp. 617-621, 1990.

Cheung, Yvonne Y. et al., "A Web-Based Tutorial of Acetabular Fractures Image Analysis", www.bidmc.harvard.edu/radio...arch/CT/cheung_paper/analysis.html, site visited Dec. 10, 2002.

Cuckler, John M., "Limb Length and Stability in Total Hip Replacement," Hip Arthroplasty: Avoiding Pitfalls, Managing Problems, Sep. 2005.

David Hebert et al. "Effect of Pelvic Depth and Pelvic Width Measurement on Hip Kinematics and Kinetics", Shriners Hospital for Children, Springfield, MA 01104.

D'Lima, Darryl D. et al., "Standard for Hip Joint Coordinate System Recommendations from the ISB Standardization Committee," pp. 1-8, Jul. 17, 2000.

Ebraheim, Nabil, et al., "Correlation Between Symphesis Pubis' Opening and SIJ's Opening During Open Book Injury" Biomechanics Laboratory, Department of Mechanical, Industrial and Manufacturing Engineering, University of Toledo, Toledo, Ohio.

Goldstein, Wayne M. et al. "Leg Length Inequality in Total Hip Arthroplasty" Orthopedics, Sep. 2005, vol. 28, No. 9/Supplement.

Gorton, George et al. "Assessment of the Kinematic Variability Between Twelve Shriners Motion Analysis Laboratories Part 2: Short term follow up" Shriners Hospital for Children, Springfield, MA, Gait and Posture 13(3):247, 2001.

http://isb.ri.ccf.org/biomch-1/archives/biomch-1-1991-06/00013.html, site visited Dec. 9 2002, Pelvic Orientation.

Kiefer, Hartmuth et al. OrthoPilot Total Hip Arthroplasty Workflow and Surgery, Orthopedics, Oct. 2005, vol. 28, No. 10/Supplement, Department of Orthopaedic and Trauma Surgery at Lukas Hospital.

Kirkwood, R.N. et al. "Radiographic and Non-Invasive Determination of the Hip Joint Center Location: Effect on Hip Joint Angles," Canadian Society for Biomechanics-American Society of Biomechanics, Aug. 14-18, 1998 http://ash-bimech.org/onlineabs/NACOB98/23/, site visited Dec. 9, 2002.

Konyves, A. et al. "The Importance of Leg Length Discrepancy After Total Hip Arthroplasty," The Journal of Bone and Joint Surgery, vol. 87-B, No. 2, Feb. 2005.

Lazovic, Djorgje et al. "Results with Navigated Bicontact Total Hip Arthroplasty" Orthopedics, Oct. 2005, vol. 28, No. 10/Supplement.

Lyon, Thomas et al., "Anterior Placement of a Pelvic Stabilizing Clamp: An Anatomical Evaluation of Danger Areas and Comparison of Placement Sites in Normal and Fractured Cadaveric Pelvi" http://www.aaos.org/wordhtml/anmeet99/poster/340.htm, AAOS On-Line Service—1999, site visited Dec. 9, 2002.

Marchinda, David et al., "A Comparison Study of Hip Joint Center Location Models," Center for Human Kinetic Studies, Mary Free Bed Hospital and Rehabilation Center, Grand Valley State University, Grand Rapids, MI, http://www.mfbrc.com/MAC/MACHj%20compare.htm, site visited Dec. 9, 2002.

Matsuda et al., "A Simple Method to Minimize Limb-Length Discrepancy After Hip Arthroplasty", Taylor & Francis 2006, Acta Orthopaedica 77 (3):375-379, Informa Healthcare, Jun. 1, 2006.

Murphy, Stephen B. Murphy et al., "Acetabular Dysplasia in the Adolescent and Young Adult," Department of Orthopaedic Surgery, Children's Hospital Medical Center and Massachusetts General Hospital, Boston, MA, Presented at 18th Open Scientific Meeting of the Hip Society, Feb. 11, 1990.

Notification of Transmittal of the International Search Report and the Written Opinion of the International Searching Authority, or the Declaration, International Filing Date: Feb. 12, 2007, International application No. PCT/US2007/003831, Applicant: Stephen B. Murphy, Date of Mailing: Jul. 30, 2007, all pages.

Prasad, Srinivas et al., "Minimally-Invasive Approach to Pelvic Osteolysis" Presentation, May 10, 2001.

Piazza, Stephen J. et al., "Determinants of the Accuracy of the Functional Method of the Hip Joint Center Location," Center for Locomotion Studies and Departments of Kinesiology.

Ranawat et al., "Correction of Limb-Length Inequality During Total Hip Arthroplasty," *The Journal of Arthroplasty* 16:715-720, Churchill Livingstone, Sep. 2001.

Sarin, Vineet K. et al., "Accurate Femur Repositioning is Critical During Intraoperative Total Hip Arthroplasty Length and Offset Assessment," Kinamed Navigation Systems LLC, Camarillo, California and Alta Orthopaedics, Santa Barbara, CA, Elsevier Inc., The Journal of Arthroplasty, vol. 20, No. 7, Oct. 2005.

Seidel, Geoffrey K. et al. "Technical Note Hip Joint Center Location From Palpable Bony Landmarks—A Cadaver Study", J. Biomechanics, vol. 28 No. 8 99. 995-998, Elsevier Science Ltd. Aug. 1995.

Starr, Roland et al., "A New Model of Three Dimensional Trunk Kinematics" Hugh Williams Gait Laboratory, Royal Children's Hospital, Parkvill, VIC, Australia, Apr. 2000.

"Sulzer Orthopedics Joint Care/ Fracture Care, Converge Porous Acetabular System Surgical Technique" Sulzer Medica, Sulzer Orthopedics Inc. Dec. 2002, Austin, TX.

Terry, Michael A. et al. "Measurement Variance in Limb Length Discrepancy: Clinical and Radiographic Assessment of Interobserver and Intraobserver Variability" Lippincott Williams & Wilkins, J. Pediatr Orthop vol. 25, No. 2, Mar./Apr. 2005.

Trousdale, Robert T. et al., "Nonarthroplastic Treatment of Hip Dysplasia in Adults" Hospital Physician, Orthopaedic Surgery Board Review Manual, Orthopaedic Surgery vol. 6, Part 1, Turner White Communications, Inc. Mar. 2000.

Vineet K. Sarin, et al., "Accurate Femur Repositioning is Critical During Intraoperative Total Hip Arthroplasty Length and Offset Assessment" Kinamed Navigation Systems LLC, Camarillo, California and Alta Orthopaedics, Santa Barbara, CA, Elsevier Inc., Oct. 2005.

Wixon et al., "Total Hip Arthroplasty a Minimal Posterior Approach Using Imageless Computer-Assisted Hip Navigation," *The Journal of Arthroplasty* 20:51-56, Elsevier Inc., Oct. 2005.

Woolson, MD, Steven T., "Leg Length Equalization During Total Hip Replacement," Orthopedics, vol. 13 No. 1, Jan. 1990, pp. 1-5.

Woolson, et al., "Results for a Method of Leg-Length Equalization for Patients Undergoing Primary Total Hip Replacement," *The Journal of Arthroplasty* 14:159-164, Churchill Livingstone, Feb. 1999.

* cited by examiner

SYSTEM AND METHOD FOR FACILITATING HIP SURGERY

CROSS-REFERENCE TO RELATED APPLICATIONS

The present application is a divisional of commonly assigned copending U.S. patent application Ser. No. 11/351,455, which was filed on Feb. 10, 2006, now U.S. Pat. No. 7,885,705, by Stephen B. Murphy for a SYSTEM AND METHOD FOR FACILITATING HIP SURGERY and is hereby incorporated by reference.

BACKGROUND OF THE INVENTION

1. Field of the Invention

The invention relates to surgical systems and methods and, more particularly, to a system and method for facilitating hip surgery.

2. Background Information

Hip arthritis due to malformations, fractures and diseases constitutes a major source of disability. Reconstruction of the hip, whether involving first time hip replacement or replacement of failed components, is complicated by the great mobility of the hip joint and the uncertainty in the exact position of pelvis and femur during surgery. When a hip joint is replaced, as in total hip arthroplasty or hip resurfacing arthroplasty, critical factors to assess include changes in leg length, offset, and anterior-posterior position. Leg length refers to the longitudinal extent of the leg, and may be measured, e.g., from a location on the pelvis down to some location along the leg, such as a point of the femur. Offset refers to the lateral dimension through the hip. This lateral dimension having contributions from changes during the reconstruction on both the pelvic and the femoral sides. Further, changes in anterior-posterior (AP) position of the joint may be measured along a third orthogonal axis.

Changes in leg length, offset and AP position following surgery can lead to a loose and unstable joint, exposing the patient to a risk of dislocation and revision, i.e., corrective surgery. Unequal leg lengths can also lead to trunkal imbalance, excessively tight tissues, and discomfort.

Typically, changes in leg length, offset and AP position are checked during total hip arthroplasty, for example, following a "trial reduction". That is, a trial stem is driven into the femur, a trial head is attached to the stem, and a trial acetabular liner is typically inserted into the prosthetic metal acetabular cup that has been inserted into the socket of the pelvis. The femoral trial components are then "reduced" into the acetabular components, i.e., temporarily assembled together. During this trial reduction, critical parameters, such as leg length, offset, AP position, the hip's free range of motion and its stability, are assessed to determine if the goals of the reconstruction are being achieved. If so, the trial prosthesis components are then replaced with the final prosthesis components.

Several systems and methods currently exist to determine changes in leg length, offset and AP position. For example, rulers and gauges exist to physically measure changes in leg length in particular. Such physical measurements, however, are often inaccurate. Another method is to use preoperative images and to plan component selection and placement to optimize leg length and offset. During surgery, the components are placed so as to be as close as possible to the preoperative plan. Other techniques involve the taking of images during the operation, such as X-rays, but these images are typically of unknown magnification, may not have been taken in the correct plane, and often do not show both legs on the same image, limiting the surgeon's ability to compare one side to the other.

Further attempts at measuring changes in leg length, offset, and AP position have involved computer-assisted surgical navigation techniques. Surgical navigation currently involves tracking the positions of the bones using optical or electromagnetic tracking systems. Typically, position tracking frames or devices are affixed to the bone to be tracked and then a coordinate system for that bone is established so that the tracking frames then track the coordinate system itself. The coordinate system of the pelvis is typically determined by finding three landmarks. These are the two anterior superior iliac spines and the pubic symphysis.

Progression of the art has stalled though because proper establishment of a femoral coordinate system requires calculation of the center of rotation of the hip. U.S. Pat. No. 6,711,431, for example, describes a non-imaging navigation system for hip replacement surgery. With this system, a center of rotation of the hip is found before reconstruction is performed in order to determine leg length and offset. After the trial prosthetic components are installed, the system requires that the new center of rotation of the hip be determined in order to calculate a change in leg length and a change in offset. Unfortunately, the hip joint that is being reconstructed is often so destroyed that such a calculation is either inaccurate or impossible to determine. It can also be time-consuming and difficult.

One attempt to circumvent this problem has been to calculate only the pelvic coordinate system and then to simply digitize a landmark somewhere on the femur that would be considered a starting point before reconstruction. The theory is that if a temporary reconstruction is performed and the same landmark is digitized, then changes in leg length, for example, could be calculated. This method, however, is imprecise due to the difficulty in bringing the leg back into the exact same position that it was in before, thereby causing the calculation to give very inaccurate information.

Accordingly, a need exists for an efficient and simplified system and method for determining changes in leg length, offset and AP position during hip surgery.

SUMMARY OF THE INVENTION

Briefly the invention relates to a system and method for use during hip surgery, such as total hip replacement surgery. The system includes position tracking frames for both the femur and the pelvis that may be removably secured to the patient during surgery. The system further includes a tracking unit and a navigation engine, which are used to establish a coordinate system at the patient's pelvis. The tracking unit may use optical, electromagnetic, or other accurate tracking methods. The navigation engine may employ image-based or image-free techniques, and is further used together with the tracking unit to capture the position and orientation of the femoral position frame relative to the pelvic position tracking frame and to the pelvic coordinate system, while the patient's leg is placed in a predetermined orientation. The system further includes an image generator configured to display one or more images for directing the surgeon to return the patient's leg to the predetermined orientation following a trial reduction based upon the previously captured orientation of the femoral position tracking frame. A leg change determination engine is also provided. Once the leg is returned to the predetermined orientation, the change in position of the femoral position tracking frame relative to the previously captured position of the femoral position tracking frame is resolved by the leg change determination engine to derive leg length, offset, and anterior-posterior (AP) position change valves. These derived values are then conveyed to the surgeon.

In use, the surgeon attaches position tracking frames to both the patient's femur and the patient's pelvis. The surgeon also utilizes the tracking unit and the navigation engine to establish a pelvic coordinate system. For example, the surgeon may removably attach one or more additional position tracking frames to the patient's pelvis and may also use a digitizing probe to identify pelvic landmarks, such as the two anterior superior iliac spines and the pubis. If desired, the pelvic coordinate system may further be established using an image-based subsystem, such as a fluoroscopic or ultrasonic images obtained at surgery, or computed tomography (CT) or magnetic resonance (MR) images obtained before or during surgery. The patient's leg is then placed in a predetermined orientation, and the navigation system captures the location of the femoral position tracking frame relative to the pelvic position tracking frame. This may be done before or after the establishment of the pelvic coordinate system. The surgeon then performs the hip procedure, such as performing a trial reduction with the insertion of a selected prosthetic stem and head into the femur and a prosthetic acetabular socket into the pelvis.

The patient's leg is then returned to the predetermined orientation. Preferably, the tracking unit, the navigation engine and the image generator all cooperate to display one or more images that guide the surgeon in returning the leg to the predetermined orientation, based upon the previously captured orientation. Once the leg is placed in the same orientation, the change in position of the reference frames compared to their original position is then purely due to linear translational changes. The leg change determination engine can therefore derive a leg length change value, an offset change value, and an AP change value. These derived values are then conveyed to the surgeon. If the derived values are not acceptable, the surgeon performs another trial reduction, e.g. by modifying the stem and head and/or the acetabular socket and directs the leg change determination engine to derive a new set of values. This process is preferably repeated until the derived change values reach acceptable levels. Significantly, the present invention does not require that a second coordinate system be established at the patient's femur, thereby substantially simplifying and reducing the time it takes to complete the hip procedure. It also avoids having to try and calculate the center of rotation of a deformed or destroyed hip joint or of the prosthetic components.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
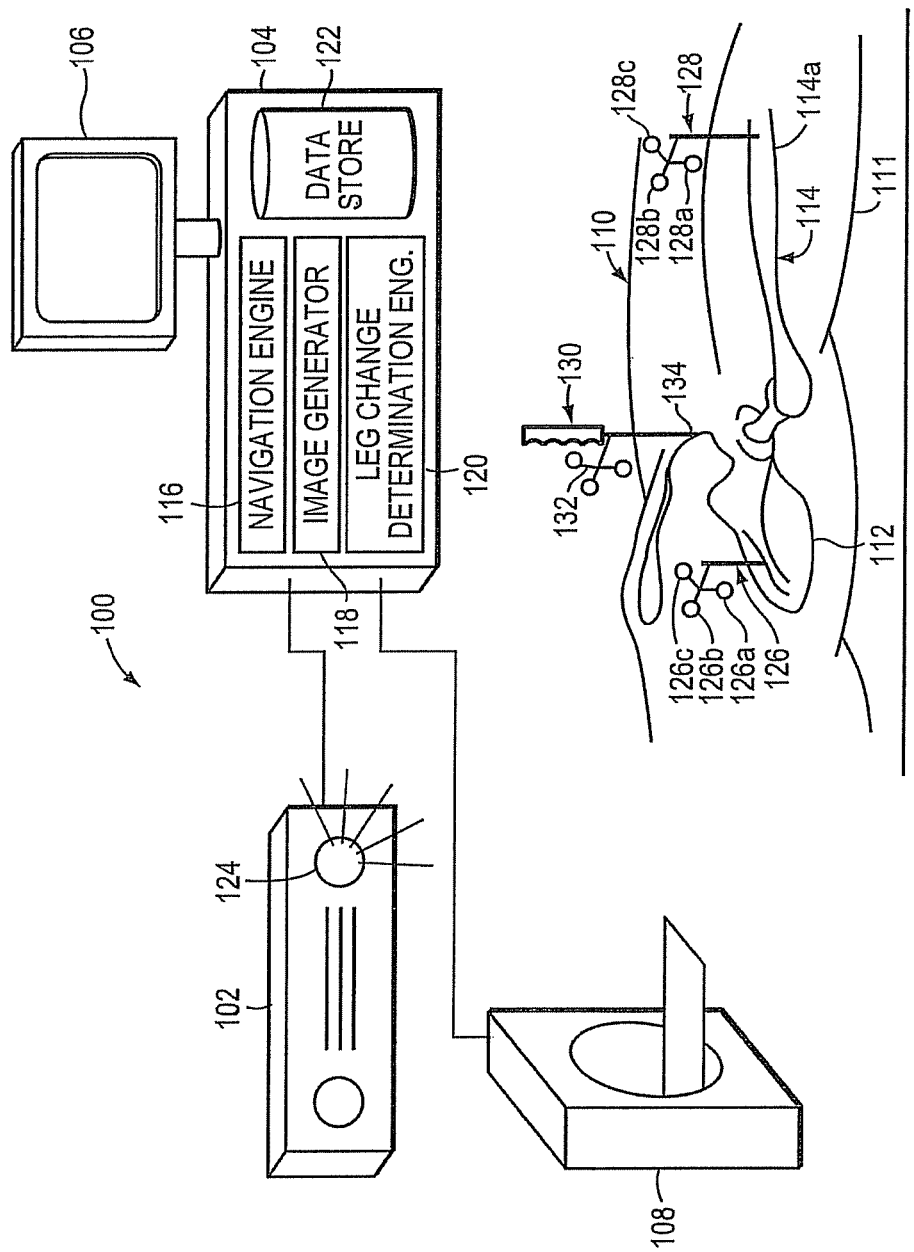
FIG. 1 is a highly schematic illustration of the system of the present invention.

FIG. 1 is a highly schematic illustration of a system 100 for assisting in the performance of hip surgery, such as a total hip replacement, in accordance with a preferred embodiment of the invention. System 100 includes a tracking unit 102 that is coupled to a base unit 104. The base unit 104 includes a display 106. The system 100 may also include an imaging device 108 similarly coupled to the base unit 104. The imaging device 108 may be a fluoroscopic device, a magnetic resonance imaging (MRI) device, a computed tomography (CT) device, an ultrasonic device, or some other suitable imaging device. The system 100 is preferably disposed in an operating room into which a patient 110, who is to undergo hip surgery, is brought. The patient 110 has a leg 111, pelvis 112 and a femur 114, which are to be operated on.

The base unit 104 has a number of subcomponents including a navigation engine 116, an image generator 118, a leg change determination engine 120 and a data store 122. The tracking unit 102 includes one or more sensors 124 that are designed, as described herein, to detect corresponding reflectors or emitters that are within its field of view. The tracking unit may use optical, electromagnetic, or other suitable tracking methodologies.

Suitable tracking systems are commercially available from Northern Digital Inc. of Waterloo, Ontario, Canada, among other suppliers.

In the illustrative embodiment, the base unit 104 is a computer, such as a personal computer (PC) or a workstation, having one or more processors, bus structures, memories, and input/output (I/O) interfaces. In addition, the navigation engine 116, image generator 118 and leg change determination engine 120 are preferably software modules or libraries containing program instructions pertaining to the methods described herein. The program instructions are stored in a computer readable memory, such as data store 122, and are executable by one or more processing elements. Other computer readable media, such as optical media, may also be used to store and execute the program instructions. Nonetheless, those skilled in the art will recognize that various combinations of software and hardware, including firmware, may be utilized to implement the present invention.

Figure 2A:
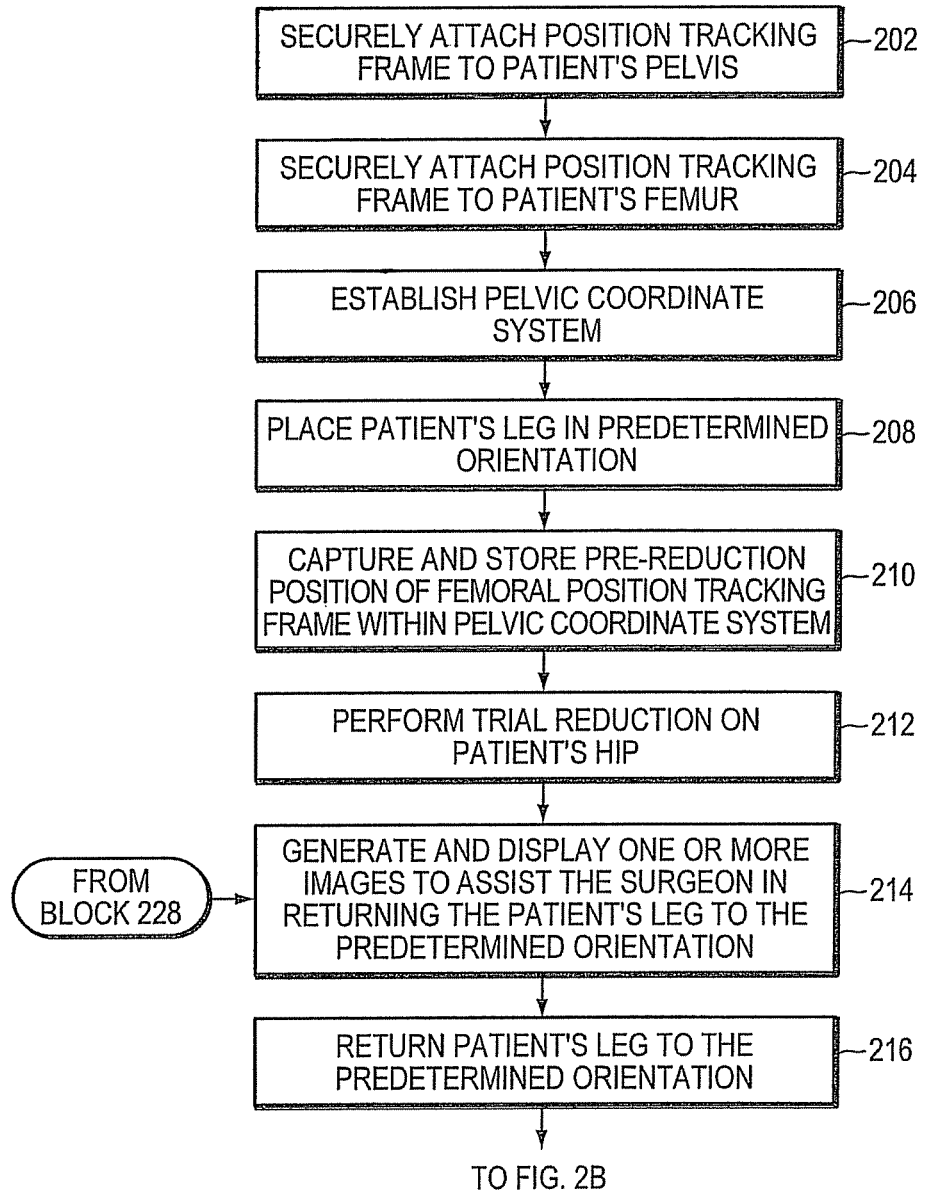
FIGS. 2A-B is a flow diagram of the methods of the present invention.
Figure 2B:
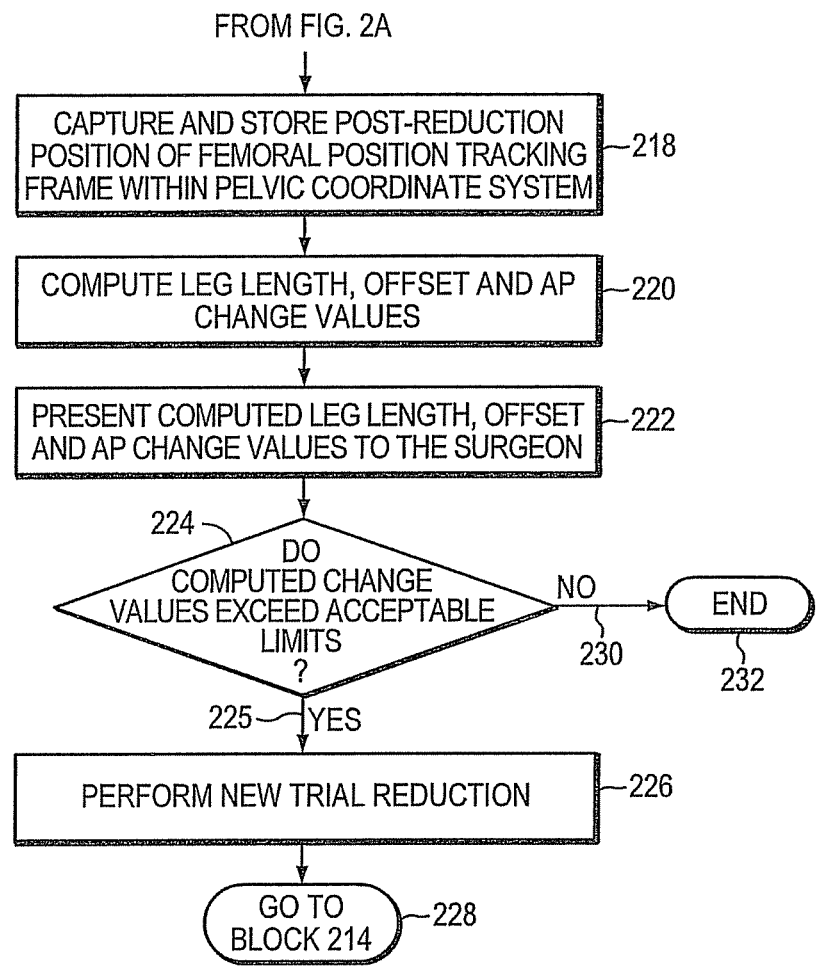

FIGS. 2A-B is a flow diagram of the methods of the present invention. First, skeletal position tracking frames 126 and 128 are securely, but removably, attached to the patient's pelvis 112 and femur 114, respectively, as indicated at blocks 202 and 204. Each position tracking frame 126, 128 preferably includes a plurality of reflectors or emitters, such as reflective balls 126a-c, 128a-c. Alternatively, these position tracking frames may emit or measure electromagnetic fields, for example. The sensor 124 of tracking unit 102 is specially designed to detect each position tracking frame, and thus determine where in the operating room the position tracking frames 126 and 128 are located.

In a preferred embodiment, the femoral position tracking frame 128 may be attached by placing two pins (not shown) into a distal end 114a of the patient's femur 114. The femoral position tracking frame 128 is then securely attached to these two pins.

Next, a pelvic coordinate system is established, as indicated at block 206. Those skilled in the art will understand that several methods may be used to establish a pelvic coordinate system, including image-based and image free methods. The pelvic coordinate system may be established either before or after the initial relationship between the pelvic and femoral position tracking frames 126, 128 is calculated. Considering the image-free method, the pelvic coordinate system may be established at the start of the surgery. Specifically, the surgeon may use a digitizing probe 130. Probe 130 has a position tracking frame 132 and a tip 134. In particular, the surgeon places the tip 134 of the digitizing probe into contact with various pelvic landmarks, such as the left and right anterior superior iliac spines and the pubic symphysis or pubic tubercles. While the tip 134 of the digitizing probe 130 is held in contact with one of these landmarks, the sensor 124 of tracking unit 102 captures the location of the probe's position tracking frame 132, thereby capturing the location of the corresponding pelvic landmark. By placing the tip in contact with each landmark and capturing its corresponding location, a pelvic coordinate system can be established.

The patient's leg 111 is then placed in a predetermined orientation, as indicated at block 208. In the preferred embodiment, the predetermined orientation is a neutral orientation. That is, the leg is brought straight down from the hip, i.e., substantially parallel to the patient's spine. In addition, the leg is not rotated i.e., the patient's foot points in a direction substantially perpendicular to the AP plane. With the patient's leg 111 in this predetermined, neutral orientation, the location of the femoral position tracking frame 128, relative to the pelvic tracking frame 126, is captured by the tracking unit 102, and this location, which may also be referred to herein as the "pre-reconstruction location", is stored in the data store 122, as indicated at block 210. The hip procedure then proceeds or continues on with a trial reduction of the hip, as indicated at block 212. That is, the surgeon installs a prosthetic femoral stem and head into the patient's femur 114, and installs a prosthetic acetabular socket into the patient's pelvis 112. The patient's leg 111 is then returned to the same predetermined orientation.

With the image-based technique, a set of pre-operative three-dimensional (3-D) images, such as CT images of the patient's pelvis 112 and femur 114 are taken, with the imaging device 108. The images are stored at data store 122. During the procedure, the pelvic and femoral position tracking frames 126, 128 are removably secured to the patient's femur and pelvis, as described above. The patient's leg 111 is then placed in the predetermined orientation, and a pre-operative leg position measurement is taken by calculating the position of the femoral position tracking frame 128 relative to the pelvic position tracking frame 126. Next, a pelvic coordinate system is established using the tracking unit 102 and navigation engine 116. The patient's pelvis 112 and femur 114 are then disarticulated, and data points on the bone surface, often including data points within the acetabular surface itself, are obtained in order to register the patient's pelvis 112 and the pelvic coordinate system to the pre-operative 3-D data set of images. In this way, the patient's pelvis 112 is synchronized to the pre-operative images. As with the image-free technique, the hip procedure proceeds with a trial reduction of the hip, and the patient's leg 111 is then returned to the same predetermined orientation.

In the illustrative embodiment, the tracking unit 102, the navigation engine 116 and the image generator 118 cooperate to assist the surgeon in bringing the patient's leg 111 back to the same predetermined orientation.

Figure 3:
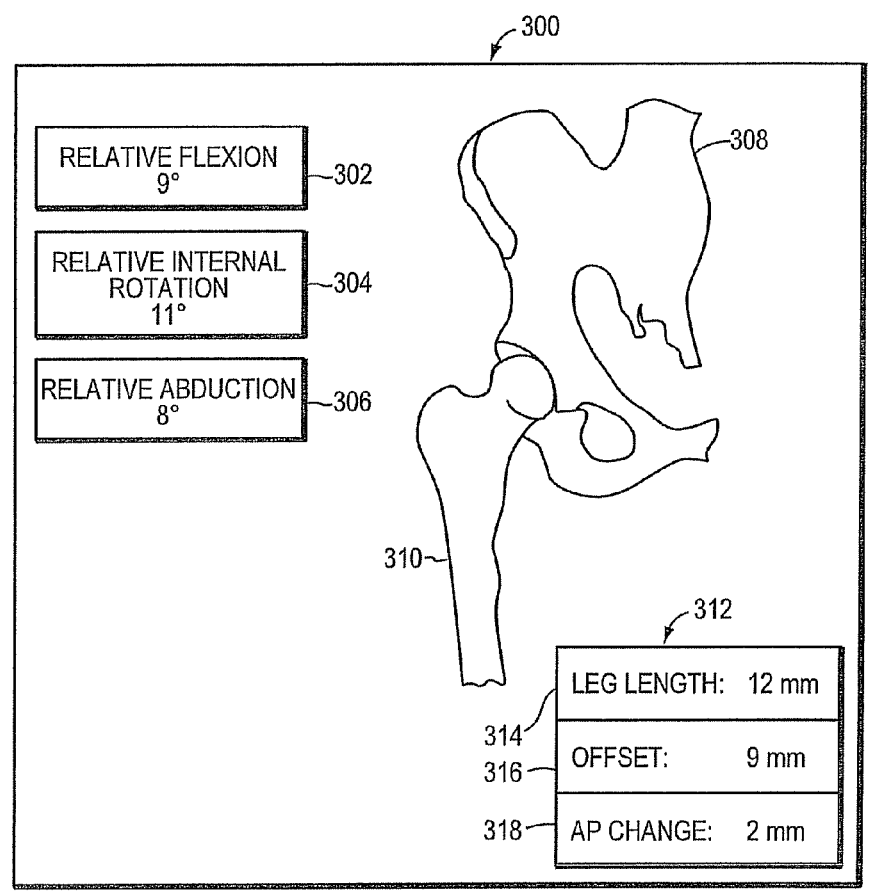
FIG. 3 is a highly schematic illustration of a display image in accordance with a preferred embodiment of the present invention.

FIG. 3 is a highly schematic illustration of a preferred format of an assisting image 300 created by the tracking unit 102, the navigation engine 116 and the image generator 118, and presented on display 106 in order to assist the surgeon in bringing the patient's leg 111 back to the predetermined orientation. Image 300 includes three display areas 302, 304 and 306 that display three respective leg orientation change values derived by the navigation engine 116 based on the current orientation of the femoral position tracking frame 128 (FIG. 1) with reference to the previously captured, pre-reconstruction orientation of the femoral position tracking frame 128. The first display area 302 displays relative flexion, preferably in degrees, between the current orientation of the patient's leg 111 and the pre-reconstruction orientation that was previously captured. That is, the tracking unit 102 monitors the femoral position tracking frame 128 as the surgeon moves the patient's leg 111 back toward the predetermined orientation, and the navigation engine 116 computes relative flexion in real-time or near real-time as the leg is being moved. As the patient's leg is moved, the relative flexion display area is updated with the value corresponding to the current orientation of the patient's leg 111 for review by the surgeon.

The second display area 304 display relative internal rotation, preferably in degrees, between the current orientation of the patient's leg 111 and the pre-reconstruction orientation that was previously captured. That is, the tracking unit 102 once again monitors the femoral position tracking frame 128 as the surgeon moves the patient's leg 111 around, and the navigation engine 116 repeatedly computes relative internal rotation in real-time or near real-time of the current orientation of the femoral position tracking frame 128 as compared to the pre-reconstruction orientation of frame 128, and this derived value is displayed in second area 304 for observation by the surgeon. As the patient's leg 111 is moved about, the relative internal rotation display area 304 is continuously updated.

The third display area 306 displays relative abduction, preferably in degrees, between the current orientation of the patient's leg 111 and the pre-reconstruction orientation. That is, as before, the tracking unit 102 monitors the femoral position tracking frame 128 as the surgeon moves the patient's leg 111 around, and the navigation engine 116 repeatedly computes relative abduction in real-time or near real-time of the current orientation of the femoral position tracking frame 128 as compared to its pre-reconstruction orientation, and this derived value is displayed in third area 306 for observation by the surgeon. As the patient's leg 111 is moved about, the computed value displayed in the relative abduction display area 304 is continuously updated.

The surgeon preferably moves the patient's leg around until the values displayed in the three areas 302, 304 and 306 each approach zero. Specifically, if the leg is oriented in more hip flexion than during the initial measurement, the display 300 will guide the surgeon into less hip flexion. Similarly, if the leg is oriented in more adduction or internal rotation than it was at the time of the initial measurement, the display 300 will guide the surgeon into less adduction or internal rotation. When all three values are zero, then the patient's leg 111 is back in the predetermined, neutral orientation.

Those skilled in the art will understand that in some cases, it may not be possible to orientate the leg 111 such that all three values are zero. In this case, the surgeon preferably orients the patient's leg 111 so that the three values are minimized and/or below some minimum threshold value, such as three or five degrees.

The display 300 may further include a schematized illustration of a pelvis 308 and femur 310. In addition to updating the values shown in display areas 302, 304 and 304, the image generator 118 may also move the femur image 310 in synch with the patient's leg 111 as it is being moved about by the surgeon.

With the patient's leg 111 back in the predetermined orientation, the current post-reconstruction position of the femoral position tracking frame 128 is captured by tracking unit 102, and its location within the pelvic coordinate system is computed by the navigation engine 116, as indicated at block 218 FIG. 2B). This computed, post-reconstruction location may also be stored in data store 122. The leg change determination engine 120 then compares the pre-reconstruction location of the femoral position tracking frame 128 with the post-reconstruction location of the femoral position tracking frame 128. Since the leg was returned to substantially the same orientation that it was in before, any changes in position of the leg would therefore be due purely to translational changes. The leg length determination engine is therefore able to compute corresponding changes in leg length, offset and/or anterior-posterior (AP), as indicated at block 220. For example, suppose that the reduction of the patient's hip with the prosthetic femoral stem and acetabular socket, result in a change in leg length of 12 millimeters (mm), a change in offset of 9 mm, and an AP change of 2 mm. In the preferred embodiment, the change values derived by the leg change determination engine 120 are preferably presented to the surgeon, as indicated at block 222.

In the illustrative embodiment, display 300 (FIG. 3) also includes a change area 312. The change area 312 includes leg length entry 314, an offset entry 316 and an AP entry 318. Within the leg length entry 314, the image generator 116 displays the computed change in leg length, i.e., 18 mm. In the offset entry 316, the image generator 116 displays the computed change in offset, i.e., 9 mm. In the AP entry 318, the image generator 116 displays the computed change in AP position, i.e., 2 mm.

Those skilled in the art will understand that the computed change values may be provided to the surgeon in other ways, such as printed out or verbalized using a synthesized voice and sound system.

The surgeon then decides whether one or more of the derived change values exceed acceptable or desired levels, as indicated by decision block 224. If so, the surgeon preferably tries a different trial reduction, e.g., by modifying the femoral head and/or the acetabular socket in an effort as to bring the change values to acceptable levels, as indicated by Yes arrow 225 leading to block 226. The process then returns to block 214, as indicated by Go To block 228. Steps 214-224 are preferably repeated until acceptable leg length, offset and AP change values are obtained. At this point, the process of the invention is complete, as indicated by No arrow 230 leading to termination block 232.

Those skilled in the art will understand that other methods besides display 300 may be used to assist the surgeon in bringing the patient's leg 111 back to the same predetermined orientation at which the initial measurement was made. For example, the navigation engine 116 and the image generator 118 may create a first, pre-reconstruction image on display 106 that shows the position of the femoral position tracking frame 128 within the pelvic coordinate system as initially captured prior to performing the trial reduction, as indicated at block 214. In addition, the tracking unit 102, the navigation engine 116 and the image generator 118 superimpose upon the first image a second, post-reconstruction image that indicates where the femoral position tracking frame 128 is currently located relative to the pelvic coordinate system, as also indicated at block 214. That is, the tracking unit 102 follows the movement of the femoral position tracking frame 128 in real-time or substantially in real-time as the patient's leg 111 is moved around by the surgeon. By monitoring the first and second images as the patient's leg 111 is moved, the surgeon can orient the patient's leg 111 so that the current, "live" image of the femoral position tracking frame 128 is aligned with the first, pre-reconstruction image of the femoral position tracking frame 128. In this way, the surgeon can bring the patient's leg 111 back to the predetermined orientation, as indicated at block 216.

It should be noted that the system and method of the present invention are able to compute leg length, offset and AP change values without having to establish a femoral coordinate system. Instead, the present invention relies on the single coordinate system, established at the patient's pelvis. Accordingly, the present invention greatly simplifies hip surgery, and yet still provides accurate leg length, offset and AP change information to the surgeon.

Those skilled in the art will further understand that other predetermined orientations may be employed.

Figure 4:
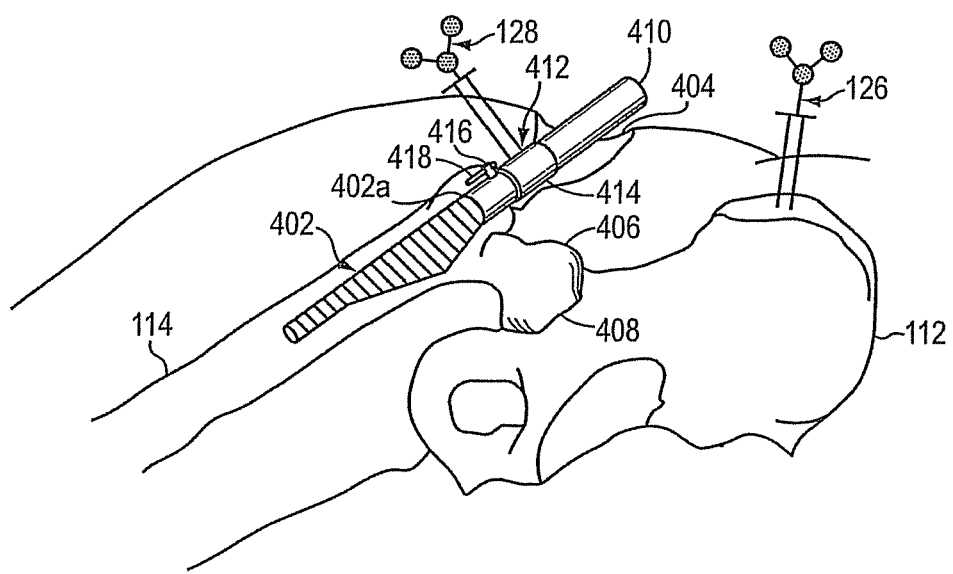
FIGS. 4 and 5 are illustrations of an alternative femoral reference frame in accordance with the present invention.
Figure 5:
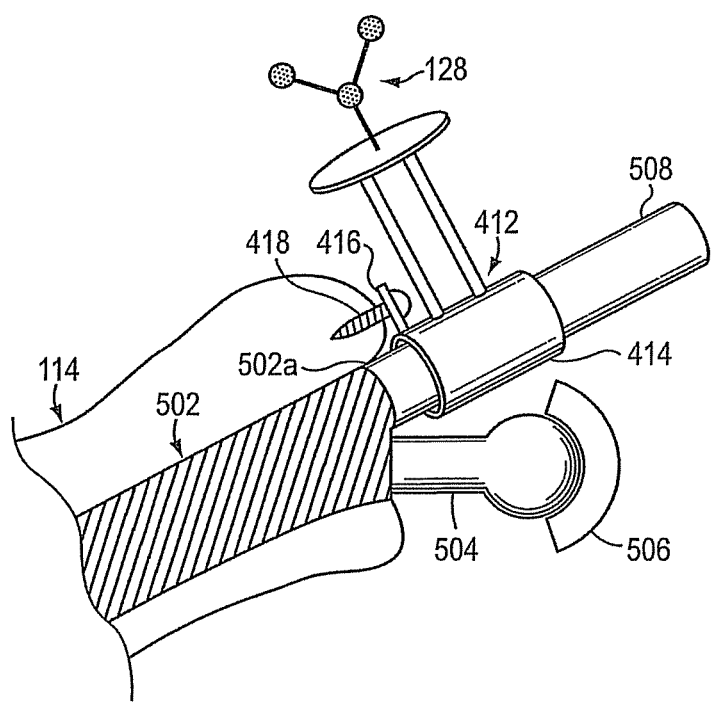

FIGS. 4 and 5 illustrate an alternative technique for attaching the femoral position tracking frame 128 to the patient's femur 114. Basically, rather than attach the position tracking frame 128 to a distal point on the femur 114, as described above, in this embodiment, the position tracking frame 128 is temporarily placed on the femur using surgical instruments through the primary incision.

In order to prepare the femur 114 for the rod-like prosthesis stem, the center of the long axis of the femur is reamed out so as to define a channel or bore within the femur. The surgeon typically uses a series of reamers, starting with small diameter reamers and moving up to larger diameter ones, to create this channel. The surgeon then uses a broach, such as an intramedullary broach, to form a more final shape of the channel.

FIG. 4 illustrates a broach 402 inserted into a channel formed in the patient's femur 114. In particular, an incision 404 is formed to provide access to the patient's femur 114, and the broach 402 is inserted into the reamed-out channel. Preferably, the femur's native head 406 is still attached to the patient's femur 114, and the native head 406 is still within the respective socket 408 on the pelvis 112. The broach 402 has a head end 402a to which a rod 410 is attached. The head end 402a of the broach 402, for example, may have a threaded bore or other rigid connection (not shown), and a first end of the rod 410 may have matching threads or other rigid connection so that the rod 410 can be firmly and reproducibly attached to the broach 402. A position tracking frame holder 412, in accordance with a preferred embodiment of the present invention, may then be slid over the rod 410 and removably secured to the patient's femur 114. The position tracking frame holder 412 includes a sleeve 414 that is sized to fit over the rod 410, such that the position tracking frame holder 412 slides along the rod 410. At an end of the sleeve 414 is a flange 416 that is rigidly attached to the sleeve 414, and adapted to abut an end of the femur 114 adjacent to the channel that was formed therein.

In the embodiment illustrated in FIGS. 4 and 5, the flange 416 is removably secured to the femur 114, thereby securing the position tracking frame holder 412 to the patient's femur 114. For example, a holding screw 418 may extend through a hole (not shown) in the flange 416 and be driven into the patient's femur 114. The holding screw 118, whose head overlies the hole in the flange 416, secures the flange 416 in position with respect to the femur 114, thereby securely attaching the holder 412 to the femur. Rigidly mounted to the sleeve 414 of the holder 412 is the femoral position tracking frame 128.

The preferred flange 416 extends away from the sleeve 414, and is substantially planar in shape, although other shapes may be used. Those skilled in the art will understand that the holder 412 may be formed from various materials.

It should be understood that the flange 416, which abuts the greater trochanter of the femur 114, essentially fixes the holder 412 in a specific location relative to the femur 114. Therefore, even though the femoral position tracking frame 128 is not directly attached to the femur, its position vis-à-vis the femur 114 is fixed.

With the holder 412 secured to the femur 114, the position of the femoral position tracking frame 128 is captured by the tracking unit 102 (FIG. 1), and its location relative to the pelvic coordinate system is derived and stored.

The procedure then continues with the surgeon removing the femur's native head 406, and replacing the first broach 402 with another broach that includes a trial prosthesis head. The surgeon also installs a trial acetabular cup within socket 408.

FIG. 5 illustrates the patient's femur 114 with the new broach 502 and trial prosthesis head 504. The trial prosthesis head 504 is reduced, i.e., placed in a trial prosthesis acetabular cup 506. Again, a rod 508 is attached to an end 502a of the broach 502, and the holder 412 is slid over the rod 508. Holder 412 is slid down the length of the rod 508 until the flange 416 again contacts the femur 114 in substantially the same place that it was contacted during the pre-reconstruction assessment, e.g., the tip of the greater trochanter. The holding screw 418 is again driven into the femur 114 to hold the holder 412 in place. With the holder 412 in place, the tracking unit 102 (FIG. 1) and navigation engine 116 follow the femoral position tracking frame 128 in at least near real-time to guide the surgeon in returning the patient's leg to the predetermined orientation, as described before. With the patient's leg back in the predetermined orientation, leg length change, offset change, and AP change values are derived and provided to the surgeon, as also described before. If these values are within acceptable limits, the holder 412 and rod 508 are removed, and the surgeon then replaces the trial prosthesis components 502, 504 and 506 with the final prosthesis components (not shown). It should be understood by those skilled in the art that this technique is not attempting to track the broach within the femur, but rather the femur itself.

Figure 6:
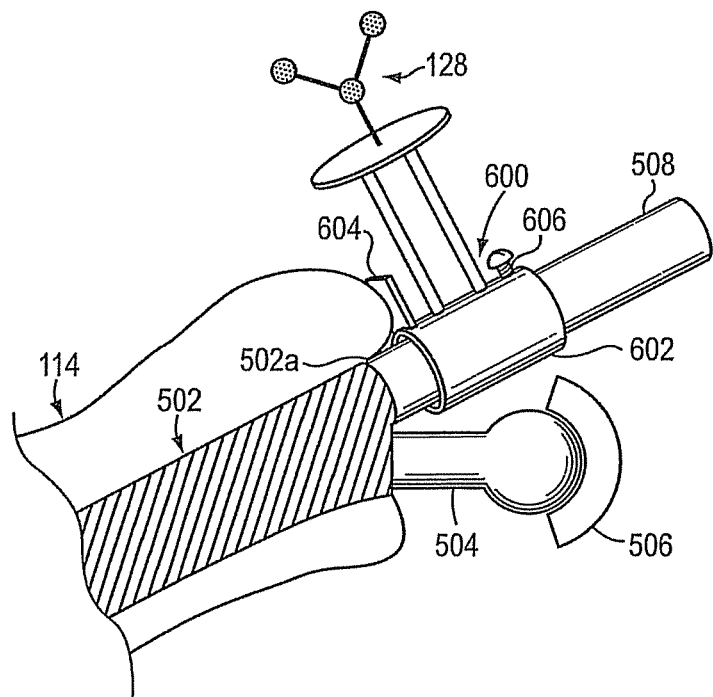
FIG. 6 is an illustration of yet another alternative femoral reference frame.

FIG. 6 illustrates an alternative embodiment of a position tracking frame holder. In this embodiment, rather than using a holding screw to secure the holder to the patient's femur, a set screw is used to secure the holder to the rod once the flange has contacted the desired landmark on the patient's femur. More specifically, a position tracking frame holder 600 includes a sleeve 602 adapted to slide over rods 410 and 508. A flange 604 is rigidly attached to and extends away from the sleeve 602. A set screw 606 extends through a hole (not shown) formed in the sleeve 602 and, when tightened, bears against the respective rod, i.e., rod 410 or 508, thereby securing the holder 600 in place. Rigidly mounted to the sleeve 602 is the femoral position tracking frame 128.

Before reconstruction is performed and preferably while the femur's native head is still attached, the holder 600 is slid over and down rod 410 (FIG. 4) until flange 506 abuts against a femoral landmark. With the flange 604 up against the femoral landmark, the set screw 606 is tightened, thereby fixing the holder 600 to the rod 410, hence fixing the holder 600 and the frame 128 relative to the patient's femur 114. The tracking unit 102 (FIG. 1) and navigation engine 116 can then capture and store the position of the frame 128 with regard to the pelvic position tracking frame 126 and/or the pelvic coordinate system.

The set screw 606 is then released and the holder 600 is removed. The surgeon continues with the procedure, and attaches the selected prosthesis head 504 to the broach 502, and places it in trial prosthesis acetabular cup 506. As necessary, rod 508 is also attached to the broach 502. As shown in FIG. 6, the holder 600 is then slid over and down rod 508 until the flange 604 once again abuts the same femoral landmark. At this point, the set screw 606 is tightened holding the holder 600 and the frame 128 in place with respect to the patient's femur 114.

As described above, the tracking unit 102 and navigation engine 116 follow the frame 128 as the surgeon returns the patient's leg to the predetermined orientation, and the image generator 118 displays one or more images to assist the surgeon in this process. With the patient's leg back in the predetermined orientation, changes in leg length, offset and AP position are derived, based on the current position of the frame 128 and its previously captured, pre-reconstruction position. This information is then provided to the surgeon, as also described before. If these values are within acceptable limits, the holder 600 and rod 508 are removed, and the surgeon then replaces the trial prosthesis components 502, 504 and 506 with the final prosthesis components (not shown).

The foregoing has been a detailed description of illustrative embodiments of the invention. Various modifications and additions can be made without departing from the spirit and scope thereof. In addition, modifications can be made to the shape of various components. Accordingly, this description is meant to be taken only by way of example, and not to otherwise limit the scope of the invention.

What is claimed is:

1. A surgical tool for use in performing hip arthroplasty on a patient having a leg, a pelvis, and a femur, the surgical tool comprising:
   an elongated body element sized to fit within a channel formed in the femur, the elongated body element having a first end and a second end, and defining a longitudinal axis between the first end and the second end;
   a support arm extending from the first end of the elongated body element, the support arm extending along the longitudinal axis of the elongated body element;
   a position tracking unit removably mounted to the support arm; and
   means for removably securing the position tracking unit in a fixed position relative to the femur, while the position tracking unit is mounted to the support arm,
   wherein the elongated body element is either
      a broach for shaping the femur to receive a prosthesis having an acetabular head, or
      a trial femoral component.

2. A surgical tool according to claim 1 in which said support arm is an extension of said elongated body element.

3. A surgical tool according to claim 1 in which said support arm is separable from said elongated body element but connectable thereto.

4. A surgical tool according to claim 3 in which said support arm is connectable to said elongated body element by interfitting threaded portions on said elongated body element and said support arm, respectively.

5. A surgical tool according to claim 1 further comprising:
   a sleeve sized to slide over said support arm, wherein said position tracking unit is attached to said sleeve.

6. A surgical tool according to claim 5 wherein said means for removably securing fixes said sleeve in the fixed position relative to the femur.

7. A surgical tool according to claim 6 further comprising a post mounted on said sleeve, the post abutting against the femur when said elongated body element is inserted into the femur.

8. A surgical tool according to claim 6 further comprising a post mountable on said femur, and a screw holding said fastener against said femur.

9. A surgical tool according to claim 6 further comprising a screw threadably extensible through said sleeve to said femur.

10. A surgical tool comprising:
    an elongated body element having a longitudinal axis,
a first end sized to fit within a channel formed in a femur of a patient,
a second end opposite the first end, and
a support arm disposed at the second end of the elongated body element, the support arm extending along the longitudinal axis beyond the femur when the first end is fitted within the channel formed in the femur of the patient;
a position tracking unit disposed on the support arm of the elongated body element; and
means for securing the position tracking unit in a fixed position relative to the femur when the first end of the elongated body element is fitted within the channel formed in the femur,
wherein the elongated body element is either
a broach, or
a trial femoral component.

11. The surgical tool of claim 10 further comprising a sleeve slidably engaged to the support arm, wherein the position tracking unit is attached to the sleeve.

12. The surgical tool of claim 10 wherein the means for securing includes a bracket and a screw.

13. A surgical tool comprising:
an elongated body element having
a longitudinal axis,
a body portion sized to fit within a channel formed in a femur of a patient, and
a support arm attached to the body portion, the support arm extending along the longitudinal axis beyond a greater trochanter of the femur when the body portion is fitted within the channel formed in the femur of the patient;
a holder slidably engaged to the support arm of the elongated body element;
a position tracking frame attached to the holder; and
a fastener configured to secure the holder in a fixed position relative to the femur when the body portion of the elongated body element is fitted within the channel formed in the femur,
wherein the surgical tool is either
a broach, or
a trial femoral component.

14. The surgical tool of claim 13 wherein the support arm is removably attached to the body portion of the elongated body element.

15. The surgical tool of claim 13 wherein the fastener includes a flange attached to the holder, and a set screw.

16. A surgical tool for use in performing hip arthroplasty on a patient having a leg, a pelvis, and a femur, the surgical tool comprising:
an elongated body element sized to fit within a channel formed in the femur, the elongated body element
having a first end and a second end, and
defining a longitudinal axis between the first end and the second end;
a support arm extending from the first end of the elongated body element, the support arm extending along the longitudinal axis of the elongated body element;
a position tracking unit removably mounted to the support arm; and
means for removably securing the position tracking unit in a fixed position relative to the femur, while the position tracking unit is mounted to the support arm.

17. A surgical tool comprising:
an elongated body element having
a longitudinal axis,
a first end sized to fit within a channel formed in a femur of a patient,
a second end opposite the first end, and
a support arm disposed at the second end of the elongated body element, the support arm extending along the longitudinal axis beyond the femur when the first end is fitted within the channel formed in the femur of the patient;
a position tracking unit disposed on the support arm of the elongated body element; and
means for securing the position tracking unit in a fixed position relative to the femur when the first end of the elongated body element is fitted within the channel formed in the femur.

18. A surgical tool comprising:
an elongated body element having
a longitudinal axis,
a body portion sized to fit within a channel formed in a femur of a patient, and
a support arm attached to the body portion, the support arm extending along the longitudinal axis beyond a greater trochanter of the femur when the body portion is fitted within the channel formed in the femur of the patient;
a holder slidably engaged to the support arm of the elongated body element;
a position tracking frame attached to the holder; and
a fastener configured to secure the holder in a fixed position relative to the femur when the body portion of the elongated body element is fitted within the channel formed in the femur.

* * * * *